(12) United States Patent
Drennan

(10) Patent No.: US 9,161,710 B1
(45) Date of Patent: Oct. 20, 2015

(54) DEVICE FOR MEASURING A PERSON'S TRUNK ROTATION FROM A SEATED POSITION

(71) Applicant: Fred Drennan, Ojai, CA (US)

(72) Inventor: Fred Drennan, Ojai, CA (US)

( * ) Notice: Subject to any disclaimer, the term of this patent is extended or adjusted under 35 U.S.C. 154(b) by 341 days.

(21) Appl. No.: 13/651,336

(22) Filed: Oct. 12, 2012

Related U.S. Application Data

(60) Provisional application No. 61/554,588, filed on Nov. 2, 2011.

(51) Int. Cl.
*A61B 5/103* (2006.01)
*A61B 5/117* (2006.01)
*A61B 5/11* (2006.01)
*A61B 5/00* (2006.01)

(52) U.S. Cl.
CPC ............. *A61B 5/1116* (2013.01); *A61B 5/4528* (2013.01); *A61B 5/4566* (2013.01); *A61B 5/6823* (2013.01)

(58) Field of Classification Search
CPC .. A61B 5/1116; A61B 5/6823; A61B 5/4528; A61B 5/4566
USPC .......................................................... 600/595
See application file for complete search history.

(56) References Cited

U.S. PATENT DOCUMENTS 5,935,087 A * 8/1999 Kobayashi ..................... 600/595
7,335,167 B1 * 2/2008 Mummy ........................ 600/587

* cited by examiner

*Primary Examiner* — Brian Szmal
*Assistant Examiner* — H. Q. Nguyen
(74) *Attorney, Agent, or Firm* — Plager Schack LLP

(57) ABSTRACT

A device provides a quick, easy and accurate method to measure a person's trunk rotation in a seated position. This measurement may be vital to identify, evaluate, and treat chronic low back pain (LBP) or to improve sports performance that requires trunk rotation, such as golf. The device may include a measuring arch, a bracket, a main arm, and a pole. The device may be attached to a seat, stool, chair, or the like, or the device may include a seat. To use, a subject may sit on the seat with arms out to the side. The subject may then rotate and move the pole, which may be oriented vertically, with her arm around the measuring arch.

4 Claims, 4 Drawing Sheets

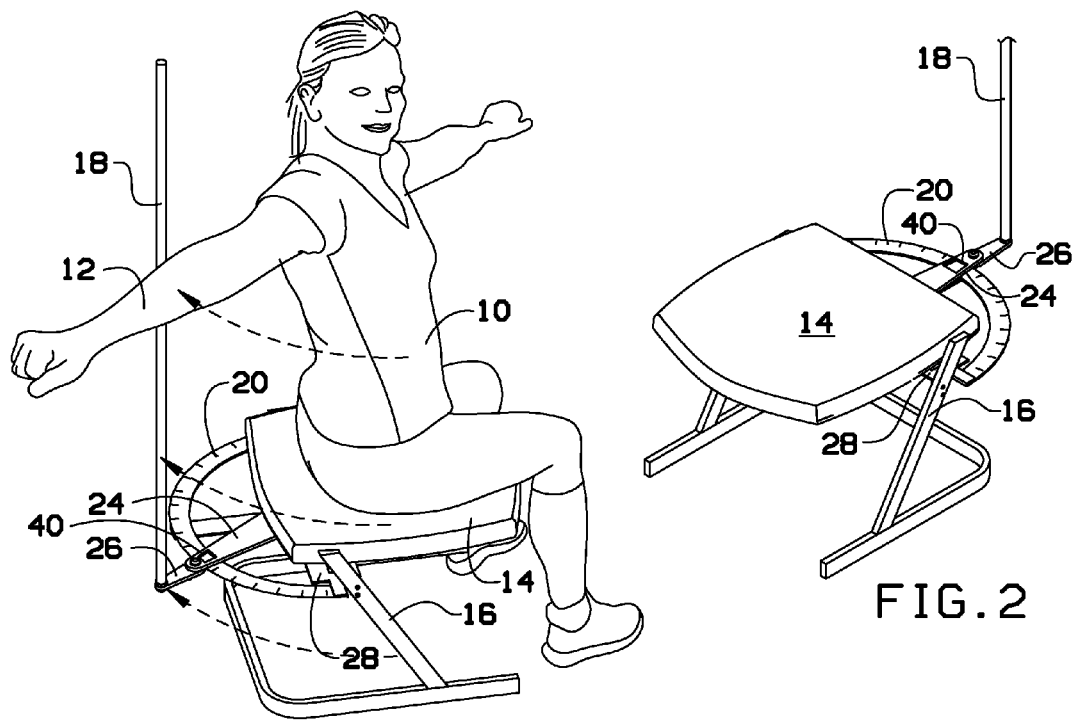
FIG. 1
FIG. 2
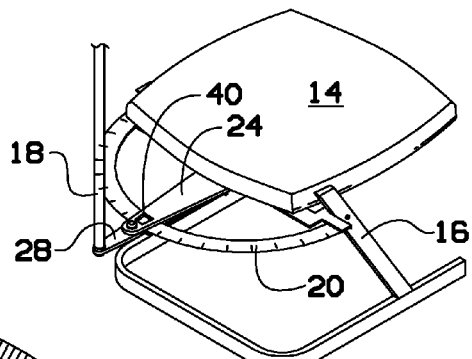
FIG. 3
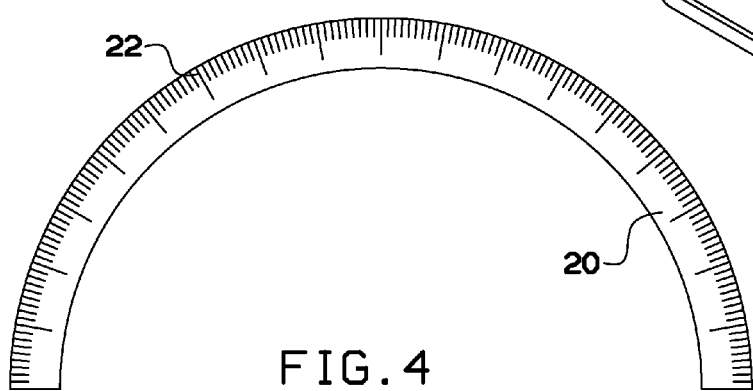
FIG. 4

DEVICE FOR MEASURING A PERSON'S TRUNK ROTATION FROM A SEATED POSITION

CROSS-REFERENCE TO RELATED APPLICATIONS

This application claims priority under 35 U.S.C. §119(e) to provisional U.S. Patent Application No. 61/554,588, filed on Nov. 2, 2011, the disclosure of which is expressly incorporated by reference herein in its entirety.

BACKGROUND OF THE PRESENT DISCLOSURE

1. Field of the Present Disclosure

The present disclosure is directed to a device and apparatus for accurately measuring a person's trunk rotation in a seated position.

2. Related Art

After headaches, back pain is the second leading cause of neurological ailments in the U.S. The cost to individuals, employers, and society is in the billions of dollars. Most acute back pain (short term) is related to trauma, such as, e.g., heavy lifting, or injury, such as, e.g., a fall. Acute back pain can usually resolve itself in days or weeks with proper treatment.

However, chronic back pain (lasting months) can have other causes (excepting disease or severe injury). In the field of physical therapy, chiropractic, and rehabilitation, one of the primary objectives to reduce chronic back pain is improving flexibility (also known as range of motion or ROM). Goniometers and inclinometers are common devices used by health care practitioners to measure a person's ROM to make proper diagnosis and measure the progress of treatment. Restricted ROM and chronic back pain are highly correlated, and improving a person's flexibility to reduce back pain is well established in the health care industry.

The field of ergonomics has greatly improved worker safety, especially in preventing musculoskeletal disorders. However, even with the best efforts in ergonomics, many jobs require employees to lift, bend, twist, and stand for long periods of time. Employers are well aware that back injuries are the leading and most costly of workers compensation claims. Employers are also aware that hiring employees with pre-existing back problems can result in costly workers compensation claims. Therefore, many employers require new hires to take physical exams that include "Functional Capacity Evaluations" where, using standardized test instruments, the individual performs various lifts, squats, and twisting movements that characterize job tasks. Comparing the test results to standardized norms, it can be determined if there is a potential for the new hire to incur an on-the-job back injury.

Workers compensation is a "no-fault" insurance program: no matter who is at fault, the employer pays. The goal of this system is provide immediate benefits to injured workers and avoid costly litigation. However, the workers compensation system is highly litigated. Disputes arise when an injured worker claims his injuries (or disabilities) are greater than what the company or the insurance company claims. In the case of a back injury, the degree of disability can make a big difference in the settlement the employee receives (and the attorney representing the employee). Beyond objective measures found in x-rays, MRIs and physical exams, a portion of the disability (the size of the settlement) is mostly subjective, determined by what the injured worker tells the treating physician what they can and cannot do. Having a standardized test instrument that would objectively measure the extent of a back disability would benefit all parties.

Flexibility is one of the five accepted components of physical fitness along with muscular strength and endurance, cardio-respiratory endurance, and body composition (fat vs. lean mass). In the world of sports, flexibility is one of the keys to athletic performance, especially in rotational sports such as golf, tennis, and batting. Even though the importance of good flexibility is well understood by athletes, measuring flexibility has been limited to the sit-and-reach box which measures only back flexion and not rotation.

SUMMARY OF THE PRESENT DISCLOSURE

The present disclosure allows a physical therapist, chiropractor, or sports trainer to consistently and accurately measure a person's trunk rotation in a seated person using a mechanical device, which results in a significant cost-effectiveness and other advantages apparent from the discussion herein.

According to one aspect of the present disclosure, a method for measuring a subject's trunk rotation includes centering the subject's axis of trunk rotation on a geometric center of a measuring arch. The method also includes raising the subject's arm, turning a main arm, adjusting a secondary arm, rotating the subject's trunk, and determining an angle. The subject's arm is raised so that it is substantially oriented with a zero mark on the measuring arch. The main arm is turned until a pole connected to the main arm contacts the subject's arm. The main arm is rotatably connected to the geometric center of the arch. The secondary arm is adjusted so that the pole contact to the subject's arm and the main arm is substantially centered on the zero mark. The secondary arm is directly connected to the main arm and the pole. The subject's trunk is rotated to a natural limit of rotation. The rotation of the trunk causes the subject's arm to push the pole, thereby rotating the main arm. The angle of the subject's trunk rotation is determined based on a position of the main arm.

According to another aspect of the present disclosure, a device for measuring a subject's trunk rotation in a seated position includes a measuring arch, a bracket, a main arm, and a pole. The bracket is connected to the measuring arch and spans the geometric center of the measuring arch. The bracket is substantially coplanar with the measuring arch. The main arm is also substantially coplanar with the bracket and the measuring arch. One end of the main arm is rotatably connected to the bracket at the geometric center of the measuring arch. A pole is connected to the other end of the main arm, and the pole is substantially perpendicular to the plane defined by the measuring arch, the bracket, and the main arm.

Additional features, advantages, and aspects of the present disclosure may be set forth or apparent from consideration of the following detailed description, drawings, and claims. Moreover, it is to be understood that both the foregoing summary of the present disclosure and the following detailed description are exemplary and intended to provide further explanation without limiting the scope of the present disclosure as claimed.

BRIEF DESCRIPTION OF THE DRAWINGS

The accompanying drawings, which are included to provide a further understanding of the present disclosure, are incorporated in and constitute a part of this specification, illustrate aspects of the present disclosure and together with the detailed description serve to explain the principles of the present disclosure. No attempt is made to show structural details of the present disclosure in more detail than may be necessary for a fundamental understanding of the present disclosure and the various ways in which it may be practiced. In the drawings:

FIG. 1 is a perspective view of a device, according to an aspect of the present disclosure, shown in use;

FIG. 2 is a forward perspective view of the device of FIG. 1;

FIG. 3 is a rear perspective view of the device of FIG. 1;

FIG. 4 is a top view of measuring arch, according to an aspect of the present disclosure;

DETAILED DESCRIPTION OF THE PRESENT DISCLOSURE

Figure 5:
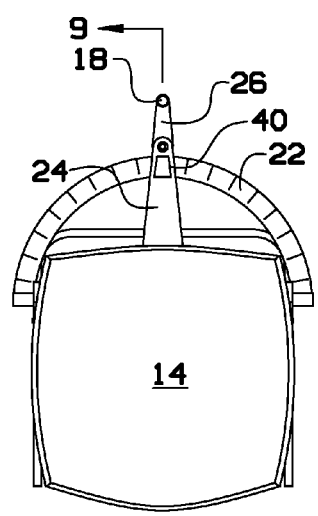
FIG. 5 is a top view of the device of FIG. 1.
Figure 6:
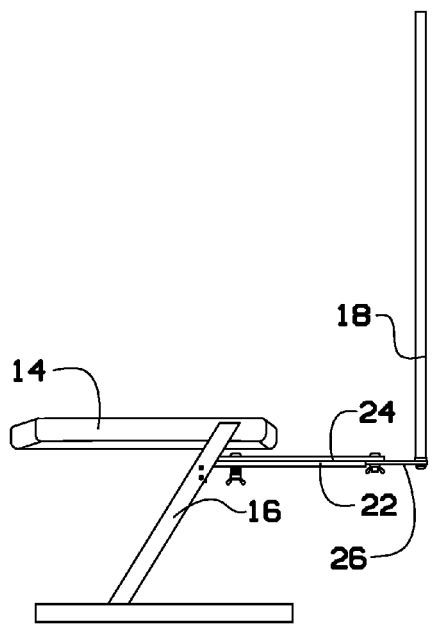
FIG. 6 is a side view of the device of FIG. 1.

The aspects of the present disclosure and the various features and advantageous details thereof are explained more fully with reference to the non-limiting aspects and examples that are described and/or illustrated in the accompanying drawings and detailed in the following description. It should be noted that the features illustrated in the drawings are not necessarily drawn to scale, and features of one aspect may be employed with other aspects as the skilled artisan would recognize, even if not explicitly stated herein. Descriptions of well-known components and processing techniques may be omitted so as to not unnecessarily obscure the aspects of the present disclosure. The examples used herein are intended merely to facilitate an understanding of ways in which the present disclosure may be practiced and to further enable those of skill in the art to practice the aspects of the present disclosure. Accordingly, the examples and aspects herein should not be construed as limiting the scope of the present disclosure, which is defined solely by the appended claims and applicable law. Moreover, it is noted that like reference numerals represent similar parts throughout the several views of the drawings.

According to an aspect of the present disclosure, a device or apparatus for measuring trunk rotation in a seated person 10 may include a measuring arch 20, a bracket 28, a main arm 24, a secondary arm 26, and a pole 18, as shown, e.g., in FIGS. 2, 3, 5 and 6. These components may be made of 12-gauge sheet metal, wood, plastic, composite, any other suitable material, or any combination thereof. The measuring arch 20, the bracket 28, the main arm 24, and the secondary arm 26 may all be substantially coplanar or lying in substantially parallel planes. The pole 18 may be substantially perpendicular to the plane(s) defined by the measuring arch 20, the bracket 28, the main arm 24, and the secondary arm 26.

The measuring arch 20 may be semicircular, with the bracket 28 spanning between the bases of the arch 20. The bracket 28 may also span, cover, or include the geometric center of the arch 20. The bracket 28 may additionally be connected to the apex of the arch 20. The bracket 28 and arch 20 may be joined by adhesives, glue, epoxy, welding, fasteners, rivets, or any other suitable means.

Figure 10:
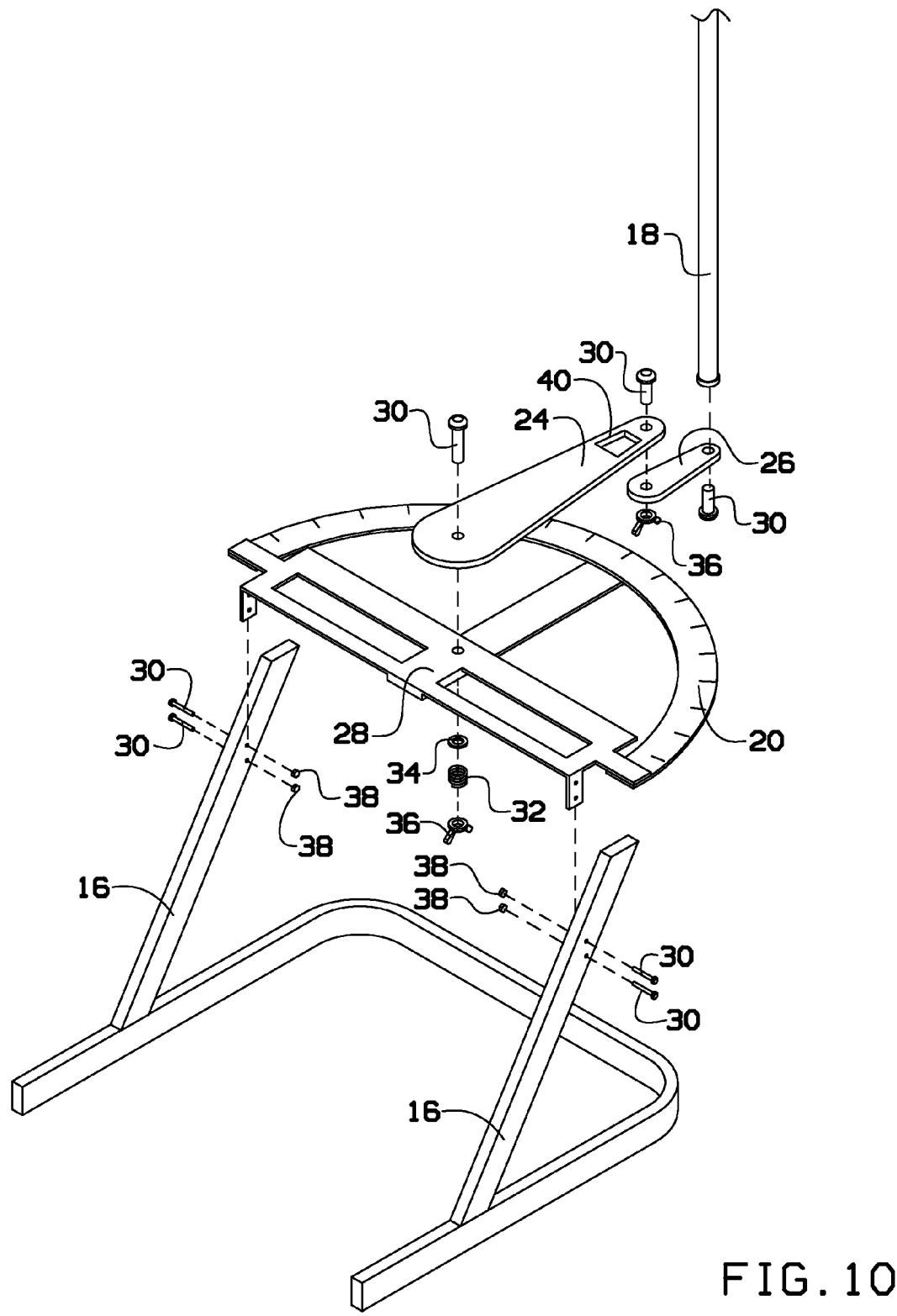
FIG. 10 is an exploded view of the device of FIG. 1.

The main arm 24 may be rotationally attached to the bracket 28 at the geometric center of the arch 20. The main arm 24 may be attached to the bracket 28 by a bolt, rivet, spinner, turntable, or any other fastener that permits the arm 24 to rotate freely relative to the arch 20. As shown in FIG. 10, for example, a bolt or fastener 30 may pass through the main arm 24 and the bracket 28. A low-friction nylon washer 34 and a tension spring 32 may fit over the fastener 30 and be held in place by a wing nut 36. The wing nut 36 may be turned against the tension spring until the proper pressure is applied between the main arm 24 and the bracket 28 so that the main arm 24 moves freely and easily.

As shown in FIG. 4, the outer edge of the measuring arch 20 may have one or more measurement marks 22. For example, measurement marks 22 may denote every degree of rotation along the outer edge. The marks 22 may include a large or longer mark at regular intervals. For example, a longer mark may be used to denote every ten degrees of rotation. The marks 22 may also include numerals indicating or numbering the degrees. The numerals may only be associated with longer marks. The numerals may count from each end of the arch 20 to its center. Alternatively, there may be two sets of numerals, each counting from an opposite side of the arch 20. The main arm 24 may extend past the outer edge of the measuring arch 20 and may include a cutout or window 40 for viewing the marks 22 on the measuring arch 20. The numerals may be oriented so that they can be easily read by a person standing outside the arch 20. The marks 22 and numerals may be placed on the arch 20 by silk-screening, decals, etching, or any other suitable process.

Figure 8:
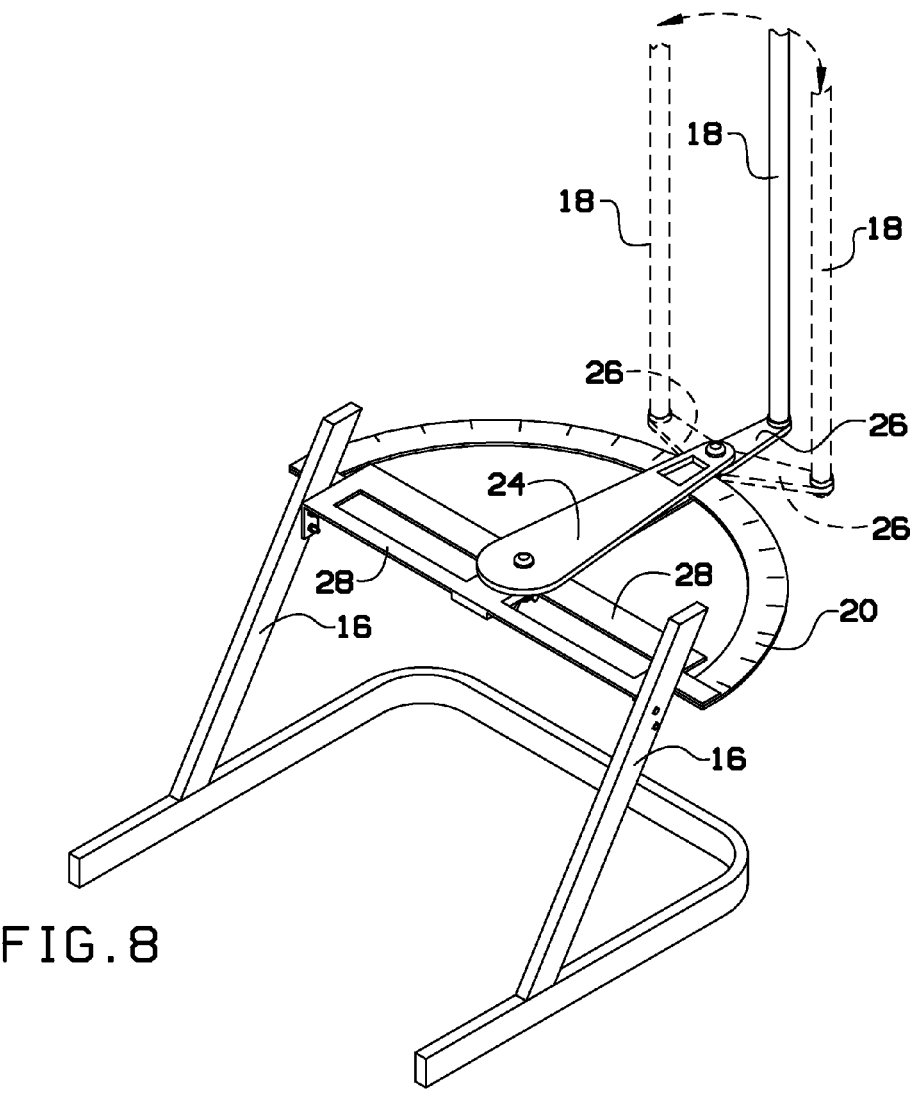
FIG. 8 is a perspective view of the device of FIG. 1 showing exemplary rotational motion of a secondary arm.

A secondary arm 26 may be attached to the end of the main arm 24. The connection may be effected by a bolt 30 and a wing nut 36, or by any other means that allows the secondary arm 26 to rotate relative to the main arm 24. As shown, e.g., in FIG. 8, the secondary arm 26 may rotate relative to the main arm 24. This may allow the device to compensate for, e.g., variations in a person's arm size, shoulder flexibility, or similar factors.

A pole 18 may be connected to the end of the secondary arm 26. The pole 18 may be substantially perpendicular to the plane(s) defined by the measuring arch 20, the bracket 28, the main arm 24, and the secondary arm 26. The pole 18 may be connected to the arm 26 with a bolt or other fastener 30. The pole 18 may include a threaded hole for receiving the fastener 30. Alternatively, the pole 18 may be attached to the arm 26 by welding, a rivet, or any other suitable means. The pole 18 may be 30 inches in lengths, although other lengths may be used without departing from the spirit and scope of the present disclosure. The pole 18 may be made from thin-walled steel tubing, wood, plastic, composites, or any other suitable material. For aspects that lack the secondary arm 26, the pole may instead be connected instead to the end of the main arm 24 as described above.

Figure 9:
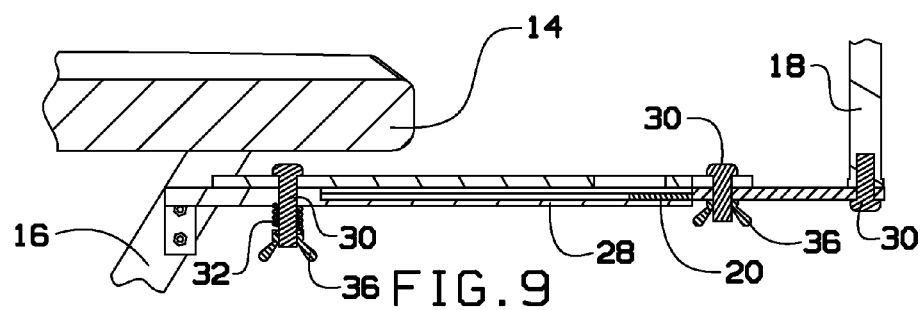
FIG. 9 is a section detail view of the device of FIG. 1 taken along line 9-9 in FIG. 5.

According to an aspect of the disclosure, the device may include a seat 14 and a seat frame 16. The bracket 28 may include vertical portions for connecting to the seat frame 16. The bracket 28 and the frame 16 may be joined using bolts 30 and nuts 38. Alternatively, the bracket 28 and the frame 16 may be joined using rivets, welding, or the like. Instead of joining to a frame 16, the bracket 28 may be equipped with adaptors (not shown) for connecting to an existing chair or stool. The seat 14 may be structured or arranged so that it is positioned above or over the geometric center of the arch 20, as shown, e.g., in FIG. 9.

Figure 7:
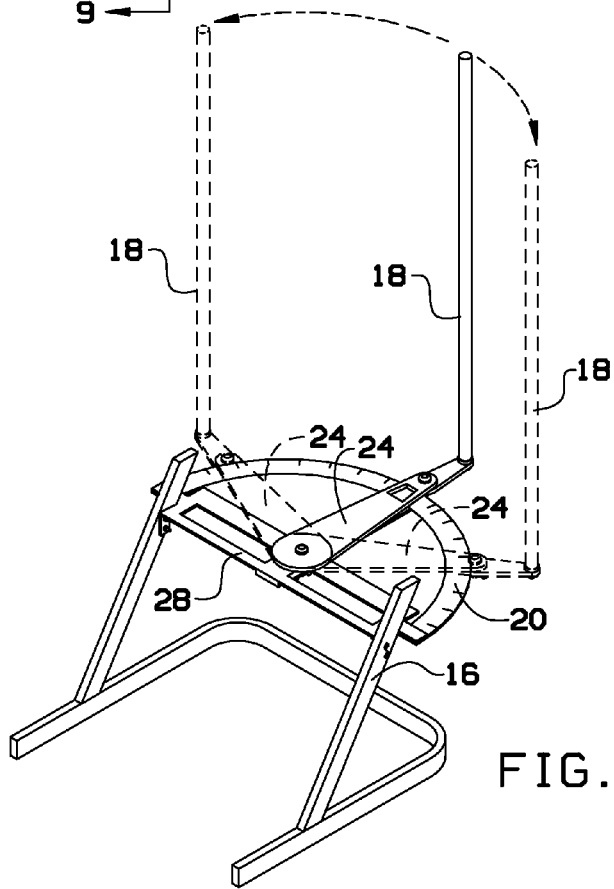
FIG. 7 is a perspective view of the device of FIG. 1 showing exemplary rotational motion of a main arm.

A view of the device in use is shown, e.g., in FIG. 1, and the rotation of the main arm 24 is shown, e.g., in FIG. 7. To use the device to measure a person's trunk rotation in a seated position, a subject 10 may be seated on the seat 14 so that the axis of rotation of her lower back may be aligned with the geometric center of the measuring arch 20. Facing forward, the subject 10 may place her arms 12 out to her sides. The operator of the device may rotate the main arm 24 so that it is as close to zero as possible. For example, the zero mark on the markings 22 may be visible through the window 40. The secondary arm 26 may be adjusted so that the main arm 24 is pointed directly at the zero mark. The subject 10 may then rotate her trunk as far as she can while continuing to hold her arms 12 out. The back of the subject's arm 12 may press against the pole 18, thereby rotating the main arm 24. After turning as far as she can, the subject 10 may return to a resting position. The angle of her rotation may be visible in the window 40. The test may be easily repeated to check for consistent readings. The test may also be repeated for the other side or arm, to test if there is any variation in trunk rotation between the subject's left and ride sides.

While the present disclosure has been described in terms of exemplary aspects, those skilled in the art will recognize that the present disclosure can be practiced with modifications in the spirit and scope of the appended claims. These examples given above are merely illustrative and are not meant to be an exhaustive list of all possible designs, aspects, applications or modifications of the present disclosure.

What is claimed is:

1. A device for measuring a subject's trunk rotation in a seated position, the device comprising:
   a frame attached to a seat wherein the frame elevates the seat from ground;
   a bracket, directly attached to the frame;
   a measuring arch, directly attached to the bracket; wherein the bracket spans a geometric center of the measuring arch, the bracket being coplanar with the measuring arch;
   a main arm comprising a first end and a second end, the main arm being coplanar with the measuring arch and the bracket, the first end of the main arm rotatably connected to the bracket at the geometric center of the measuring arch;
   a secondary arm, rotatably attached to the second end of the main arm and extending past the measuring arch; and
   a pole connected to the secondary arm, the pole being perpendicular to a plane defined by the measuring arch, bracket, and main arm;
   wherein movement of the pole about the geometric center of the measuring arch enables measurement from the measuring arch to provide the measurement about a subject's trunk rotation.

2. The device of claim 1, wherein the measuring arch comprises a plurality of measuring marks.

3. The device of claim 2, wherein at least one of the measuring marks is designated as a zero mark.

4. The device of claim 1, wherein the bracket is configured to attached to a chair, chair frame, stool, stool frame, seat, seat frame.

* * * * *